(12) United States Patent
Cao et al.

(10) Patent No.: US 11,096,638 B2
(45) Date of Patent: Aug. 24, 2021

(54) RADIATION DETECTOR

(71) Applicant: SHENZHEN XPECTVISION TECHNOLOGY CO., LTD., Shenzhen (CN)

(72) Inventors: Peiyan Cao, Shenzhen (CN); Yurun Liu, Shenzhen (CN)

(73) Assignee: SHENZHEN XPECTVISION TECHNOLOGY CO., LTD., Shenzhen (CN)

( * ) Notice: Subject to any disclaimer, the term of this patent is extended or adjusted under 35 U.S.C. 154(b) by 0 days.

(21) Appl. No.: 17/176,608

(22) Filed: Feb. 16, 2021

(65) Prior Publication Data

US 2021/0161488 A1 Jun. 3, 2021

Related U.S. Application Data

(63) Continuation of application No. PCT/CN2018/104600, filed on Sep. 7, 2018.

(51) Int. Cl.
*G01T 1/00* (2006.01)
*A61B 6/00* (2006.01)
(Continued)

(52) U.S. Cl.
CPC ......... *A61B 6/4241* (2013.01); *A61B 6/032* (2013.01); *G01N 23/046* (2013.01); *G01N 23/06* (2013.01); *G01N 23/203* (2013.01); *G01N 23/2251* (2013.01); *G01N 2223/04* (2013.01); *G01N 2223/053* (2013.01); *G01N 2223/07* (2013.01); *G01N 2223/419* (2013.01); *G01N 2223/501* (2013.01); *G01N 2223/507* (2013.01)

(58) Field of Classification Search
CPC ......... G01T 1/00; G01T 1/247; A61B 6/4241; A61B 6/032; G01N 23/046; G01N 23/203; G01N 23/2251; G01N 23/06; G01N 2223/07; G01N 2223/419; G01N 2223/053; G01N 2223/507; G01N 2223/04; G01N 2223/501
See application file for complete search history.

(56) References Cited

U.S. PATENT DOCUMENTS 7,488,945 B2 2/2009 Li et al.
2007/0206721 A1 9/2007 Tkaczyk et al.
(Continued)

FOREIGN PATENT DOCUMENTS

CN 1627100 A 6/2005
CN 101918860 A 12/2010
(Continued)

*Primary Examiner* — Jurie Yun
(74) *Attorney, Agent, or Firm* — IPro, PLLC; Qian Gu

(57) ABSTRACT

Disclosed herein is a detector, comprising: a pixel comprising a first subpixel and a second subpixel, wherein the first subpixel is configured to generate a first electrical signal upon exposure to radiation, and wherein the second subpixel is configured to generate a second electrical signal upon exposure to the radiation; wherein the detector is configured to determine a number of particles of the radiation incident on the first subpixel over a first period of time, based on the first electrical signal; wherein the detector is configured to determine an intensity of the radiation by integrating the second electrical signal over a second period of time.

26 Claims, 14 Drawing Sheets

(51) Int. Cl.
*G01N 23/203* (2006.01)
*G01N 23/2251* (2018.01)
*G01N 23/046* (2018.01)
*A61B 6/03* (2006.01)
*G01N 23/06* (2018.01)

(56) References Cited

U.S. PATENT DOCUMENTS

2010/0111248 A1 5/2010 Baeumer et al.
2020/0330058 A1* 10/2020 Cao ..................... A61B 6/4241
2021/0106296 A1* 4/2021 Cao ..................... G01N 23/10

FOREIGN PATENT DOCUMENTS

CN 102782524 A 11/2012
CN 104159051 A 11/2014

* cited by examiner

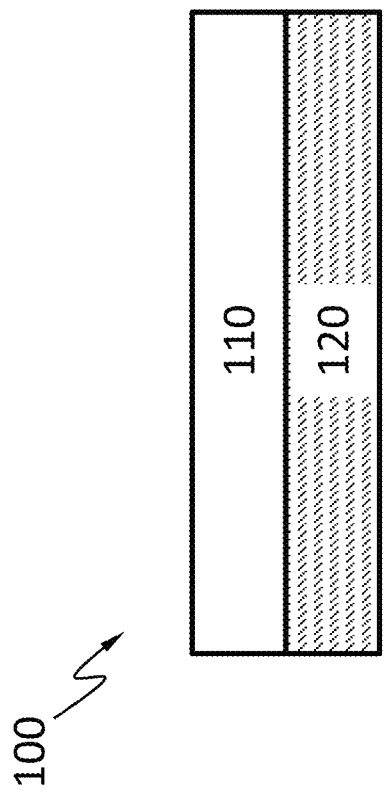

RADIATION DETECTOR

TECHNICAL FIELD

The disclosure herein relates to a radiation detector.

BACKGROUND

Radiation detectors may be devices used to measure the flux, spatial distribution, spectrum or other properties of radiation. Radiation detectors may be used for many applications. One important application is imaging. Radiation imaging is a radiography technique and can be used to reveal the internal structure of a non-uniformly composed and opaque object such as the human body.

Early radiation detectors for imaging include photographic plates and photographic films. A photographic plate may be a glass plate with a coating of light-sensitive emulsion. Although photographic plates were replaced by photographic films, they may still be used in special situations due to the superior quality they offer and their extreme stability. A photographic film may be a plastic film (e.g., a strip or sheet) with a coating of light-sensitive emulsion.

In the 1980s, photostimulable phosphor plates (PSP plates) became available. A PSP plate may contain a phosphor material with color centers in its lattice. When the PSP plate is exposed to radiation, electrons excited by radiation are trapped in the color centers until they are stimulated by a laser beam scanning over the plate surface. As the plate is scanned by laser, trapped excited electrons give off light, which is collected by a photomultiplier tube. The collected light is converted into a digital image. In contrast to photographic plates and photographic films, PSP plates can be reused.

Another kind of radiation detectors are radiation image intensifiers. Components of a radiation image intensifier are usually sealed in a vacuum. In contrast to photographic plates, photographic films, and PSP plates, radiation image intensifiers may produce real-time images, i.e., do not require post-exposure processing to produce images. radiation first hits an input phosphor (e.g., cesium iodide) and is converted to visible light. The visible light then hits a photocathode (e.g., a thin metal layer containing cesium and antimony compounds) and causes emission of electrons. The number of emitted electrons is proportional to the intensity of the incident radiation. The emitted electrons are projected, through electron optics, onto an output phosphor and cause the output phosphor to produce a visible-light image.

Scintillators operate somewhat similarly to radiation image intensifiers in that scintillators (e.g., sodium iodide) absorb radiation and emit visible light, which can then be detected by a suitable image sensor for visible light. In scintillators, the visible light spreads and scatters in all directions and thus reduces spatial resolution. Reducing the scintillator thickness helps to improve the spatial resolution but also reduces absorption of radiation. A scintillator thus must strike a compromise between absorption efficiency and resolution.

Semiconductor radiation detectors largely overcome this problem by direct conversion of radiation into electric signals. A semiconductor radiation detector may include a semiconductor layer that absorbs radiation in wavelengths of interest. When a particle of radiation is absorbed in the semiconductor layer, multiple charge carriers (e.g., electrons and holes) are generated and swept under an electric field towards electric contacts on the semiconductor layer.

SUMMARY

Disclosed herein is a detector, comprising: a pixel comprising a first subpixel and a second subpixel, wherein the first subpixel is configured to generate a first electrical signal upon exposure to radiation, and wherein the second subpixel is configured to generate a second electrical signal upon exposure to the radiation; wherein the detector is configured to determine a number of particles of the radiation incident on the first subpixel over a first period of time, based on the first electrical signal; wherein the detector is configured to determine an intensity of the radiation by integrating the second electrical signal over a second period of time.

According to an embodiment, the first period of time and the second period of time are the same.

According to an embodiment, the first subpixel abuts the second subpixel.

According to an embodiment, the detector is configured to measure energies of the particles of the radiation incident on the first subpixel, based on the first electrical signal.

According to an embodiment, the pixel further comprises a third subpixel configured to generate a third electrical signal upon exposure to the radiation; and wherein the detector is configured to determine a number of particles of the radiation incident on the third subpixel over the first period of time, based on the third electrical signal.

According to an embodiment, the detector is configured to measure energies of the particles of the radiation incident on the third subpixel, based on the third electrical signal.

According to an embodiment, the detector is configured to determine a sum of the number of particles of the radiation incident on the first subpixel and the number of particles of the radiation incident on the third subpixel over the first period of time.

According to an embodiment, the pixel further comprises a fourth subpixel configured to generate a fourth electrical signal upon exposure to the radiation; and wherein the detector is configured to determine the intensity of the radiation by integrating the second electrical signal and the fourth electrical signal over the second period of time.

According to an embodiment, the detector is configured to determine an energy spectrum of the radiation based on the energies of the particles of the radiation.

According to an embodiment, the detector further comprises an integrator configured to integrate the second electrical signal.

According to an embodiment, the first subpixel and the second subpixel are configured to operate in parallel.

According to an embodiment, the first subpixel comprises a radiation absorption layer and an electric contact; and wherein the first electrical signal is a voltage of the electric contact.

According to an embodiment, the detector further comprises: a first voltage comparator configured to compare the voltage to a first threshold; a second voltage comparator configured to compare the voltage to a second threshold; a counter configured to register the number of the particles of the radiation; a controller; wherein the controller is configured to start a time delay from a time at which the first voltage comparator determines that an absolute value of the voltage equals or exceeds an absolute value of the first threshold; wherein the controller is configured to activate the second voltage comparator during the time delay; wherein the controller is configured to cause the number registered by the counter to increase by one, when the second voltage comparator determines that an absolute value of the voltage equals or exceeds an absolute value of the second threshold.

According to an embodiment, the detector further comprises an operational amplifier integrator electrically connected to the electric contact.

According to an embodiment, the controller is configured to activate the second voltage comparator at a beginning or expiration of the time delay.

According to an embodiment, the controller is configured to determine the energies based on a value of the voltage measured upon expiration of the time delay.

According to an embodiment, a rate of change of the voltage is substantially zero at expiration of the time delay.

According to an embodiment, the radiation absorption layer comprises a diode.

According to an embodiment, the radiation absorption layer comprises silicon, germanium, GaAs, CdTe, CdZnTe, or a combination thereof.

According to an embodiment, the detector does not comprise a scintillator.

Disclosed herein is a system comprising a detector described above, and a radiation source, wherein the system is configured to perform radiation radiography on human body, limb, or teeth.

Disclosed herein is a cargo scanning or non-intrusive inspection (NII) system, comprising the detector described above, and a radiation source, wherein the cargo scanning or non-intrusive inspection (NII) system is configured for forming an image based on backscattered radiation.

Disclosed herein is a cargo scanning or non-intrusive inspection (NII) system, comprising the detector described above, and a radiation source, wherein the cargo scanning or non-intrusive inspection (NII) system is configured forming an image based on radiation transmitted through an object inspected.

Disclosed herein is a full-body scanner system comprising the detector described above, and a radiation source.

Disclosed herein is a computed tomography (radiation CT) system comprising the detector described above and a radiation source.

Disclosed herein is an electron microscope comprising the detector described above, an electron source and an electronic optical system.

BRIEF DESCRIPTION OF FIGURES

FIG. 1A schematically shows a cross-sectional view of the detector, according to an embodiment.

DETAILED DESCRIPTION

FIG. 1A schematically shows a cross-sectional view of a detector 100, according to an embodiment. The detector 100 may include a radiation absorption layer 110 and an electronics layer 120 (e.g., an ASIC) for processing or analyzing electrical signals incident radiation generates in the radiation absorption layer 110. In an embodiment, the detector 100 does not comprise a scintillator. The radiation absorption layer 110 may comprise a semiconductor material such as silicon, germanium, GaAs, CdTe, CdZnTe (CZT), or a combination thereof. The semiconductor may have a high mass attenuation coefficient for the radiation energy of interest.

Figure 1B:
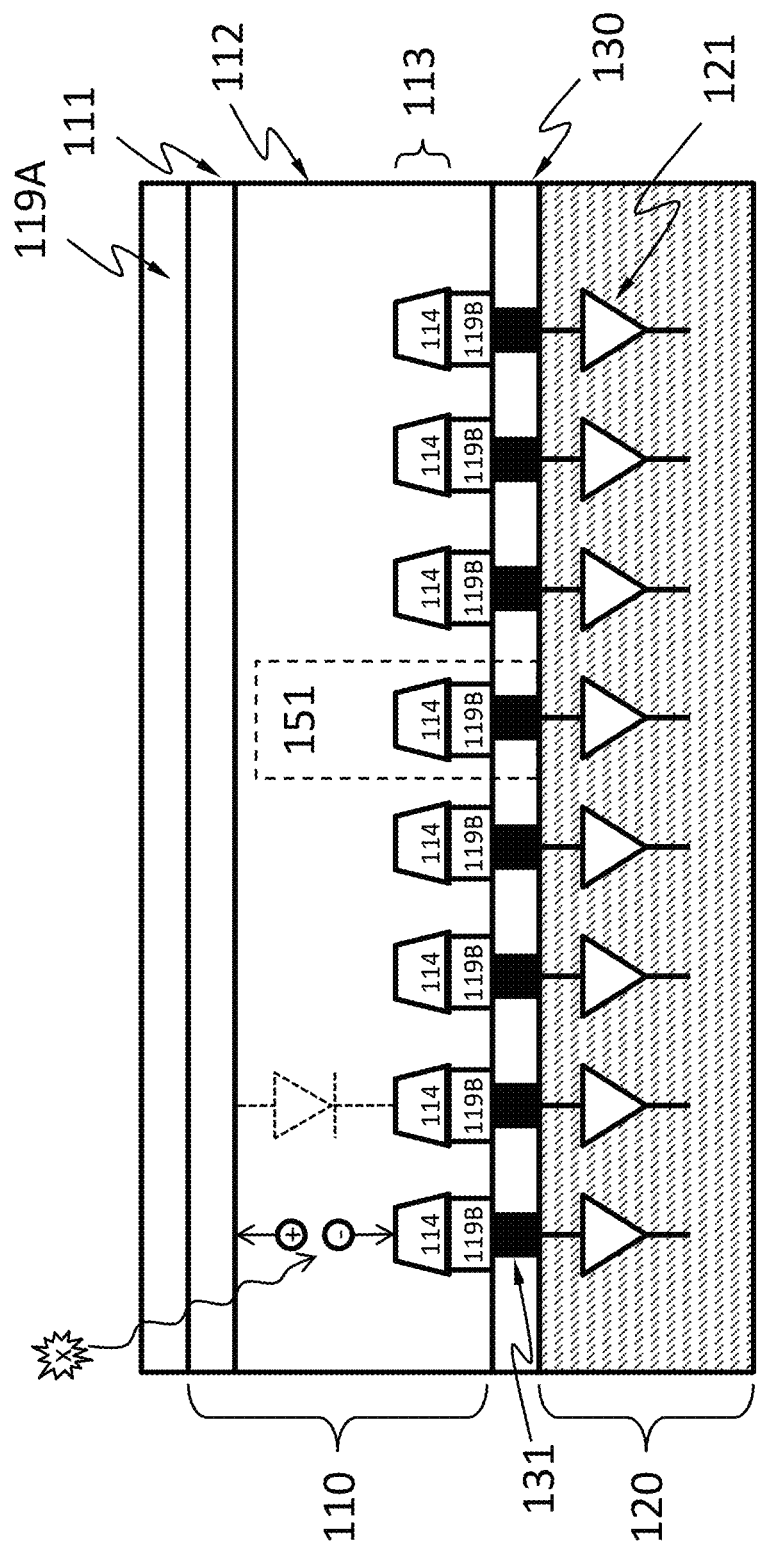
FIG. 1B schematically shows a detailed cross-sectional view of the detector, according to an embodiment.

As shown in a detailed cross-sectional view of the detector 100 in FIG. 1B, according to an embodiment, the radiation absorption layer 110 may include one or more diodes (e.g., p-i-n or p-n) formed by a first doped region 111, one or more discrete regions 114 of a second doped region 113. The second doped region 113 may be separated from the first doped region 111 by an optional intrinsic region 112. The discrete regions 114 are separated from one another by the first doped region 111 or the intrinsic region 112. The first doped region 111 and the second doped region 113 have opposite types of doping (e.g., region 111 is p-type and region 113 is n-type, or region 111 is n-type and region 113 is p-type). In the example in FIG. 1B, each of the discrete regions 114 of the second doped region 113 forms a diode with the first doped region 111 and the optional intrinsic region 112. Namely, in the example in FIG. 1B, the radiation absorption layer 110 comprises at least one diode having the first doped region 111 and an electric contact 119A as a shared electrode. The first doped region 111 and the electric contact 119A may also have discrete portions.

When a particle of radiation hits the radiation absorption layer 110 including diodes, the particle of radiation may be absorbed and generate one or more charge carriers by a number of mechanisms. A particle of radiation may generate 10 to 100000 charge carriers. The charge carriers may drift to the electric contacts of one of the diodes under an electric field. The field may be an external electric field. An electric contact 119B may include discrete portions, each of which is in electrical contact with the discrete regions 114. In an embodiment, the charge carriers generated by a single particle of radiation incident around the footprint of one of two groups of discrete regions 114 are not substantially shared by these two different groups of discrete regions 114 ("not substantially shared" here means less than 2%, less than 0.5%, less than 0.1%, or less than 0.01% of these charge carriers flow to a different group of the discrete regions 114 than the rest of the charge carriers). The area around a group of discrete regions 114 where substantially all (more than 95%, more than 98% or more than 99% of) charge carriers generated by a particle of radiation incident therein flow to the group of discrete regions 114 is called a pixel 150 associated with that group of discrete regions 114. Namely, less than 5%, less than 2% or less than 1% of these charge carriers flow beyond the pixel 150. A pixel 150 may encompass multiple subpixels 151. A subpixel 151 may be an area in the radiation absorption layer 110 around one of the discrete regions 114 in the pixel 150, where substantially all (more than 98%, more than 99.5%, more than 99.9%, or more than 99.99% of) charge carriers generated by a particle of radiation incident in the subpixel 151 flow to the discrete region 114 and the electric contact 119B connected thereto. Namely, less than 2%, less than 1%, less than 0.1%, or less than 0.01% of these charge carriers flow beyond the subpixel 151.

Figure 1C:
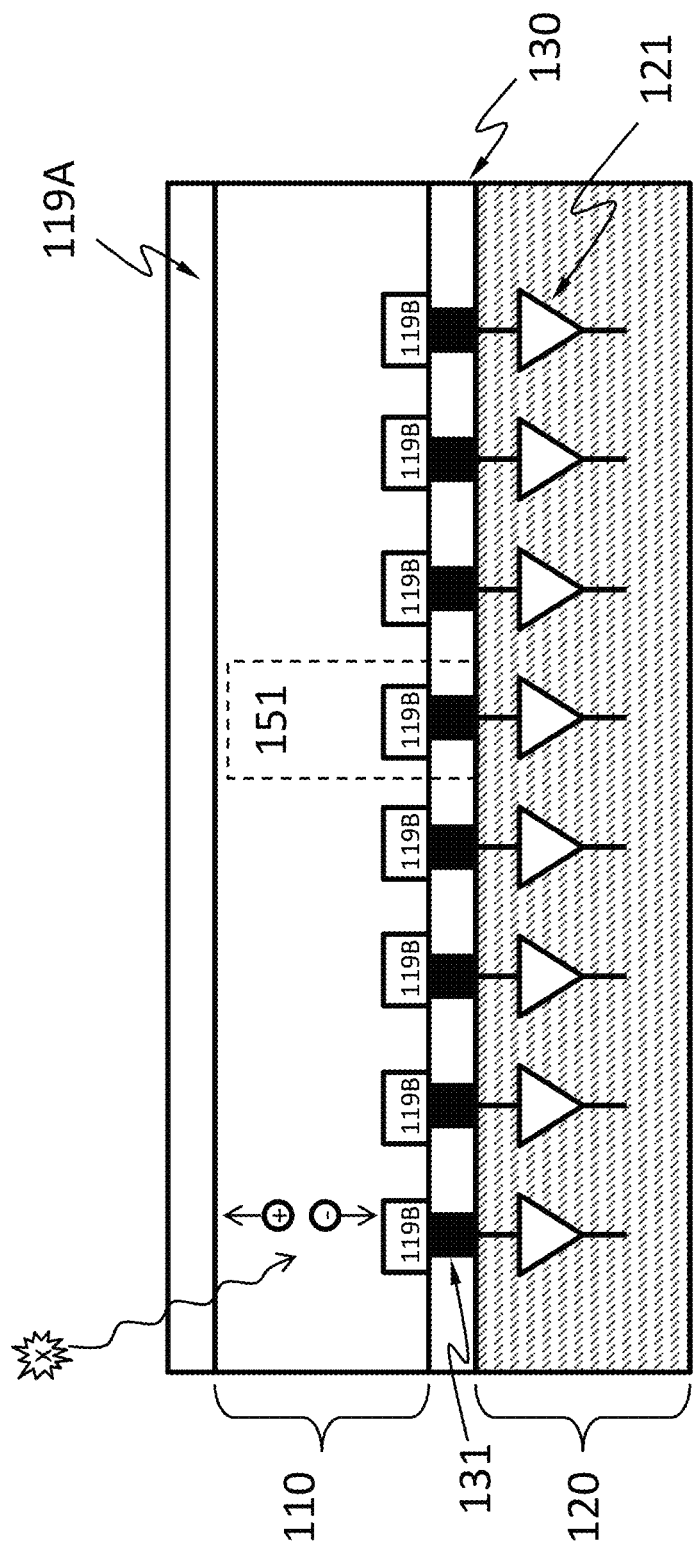
FIG. 1C schematically shows an alternative detailed cross-sectional view of the detector, according to an embodiment.

As shown in an alternative detailed cross-sectional view of the detector 100 in FIG. 1C, according to an embodiment, the radiation absorption layer 110 may comprise a resistor of a semiconductor material such as such as silicon, germanium, GaAs, CdTe, CdZnTe (CZT), or a combination thereof, but does not include a diode. The semiconductor may have a high mass attenuation coefficient for the radiation energy of interest.

When a particle of radiation hits the radiation absorption layer 110 including a resistor instead of diodes, it may be absorbed and generate one or more charge carriers by a number of mechanisms. A particle of radiation may generate 10 to 100000 charge carriers. The charge carriers may drift to the electric contacts 119A and 119B under an electric field. The field may be an external electric field. The electric contact 119B includes discrete portions. In an embodiment, the charge carriers generated by a single particle of radiation incident around the footprint of one of two groups of discrete portions of the electric contact 119B are not substantially shared by these two different groups of discrete portions of the electric contact 119B ("not substantially shared" here means less than 2%, less than 0.5%, less than 0.1%, or less than 0.01% of these charge carriers flow to a different group of the discrete portions than the rest of the charge carriers). The area around a group of discrete portions of the electric contact 119B where substantially all (more than 95%, more than 98% or more than 99% of) charge carriers generated by a particle of radiation incident therein flow to the group of discrete portions of the electric contact 119B is called a pixel 150 associated with that group of discrete portions of the electric contact 119B. Namely, less than 5%, less than 2% or less than 1% of these charge carriers flow beyond the pixel 150. A pixel 150 may encompass multiple subpixels 151. The subpixel 151 may be an area in the radiation absorption layer 110 around one of the discrete portions of the electric contact 119B, where substantially all (more than 98%, more than 99.5%, more than 99.9% or more than 99.99% of) charge carriers generated by a particle of radiation incident in the subpixel 151 flow to the discrete portion of the electric contact 119B. Namely, less than 2%, less than 0.5%, less than 0.1%, or less than 0.01% of these charge carriers flow beyond the subpixel 151.

The electronics layer 120 may include an electronic system 121 suitable for processing or interpreting signals generated by particles of radiation incident on the radiation absorption layer 110. The electronic system 121 may include an analog circuitry such as a filter network, amplifiers, integrators, and comparators, or a digital circuitry such as a microprocessor, and a memory. The electronic system 121 may include components shared by the subpixels 151 in a given pixel 150 or components dedicated to a single subpixel 151 in a given pixel 150. For example, the electronic system 121 may include an amplifier dedicated to each subpixel 151 in a given pixel 150 and a microprocessor shared among all the subpixels 151 in a given pixel 150. The electronic system 121 may be electrically connected to the subpixels 151 by vias 131. Space among the vias may be filled with a filler material 130, which may increase the mechanical stability of the connection of the electronics layer 120 to the radiation absorption layer 110.

Figure 2:
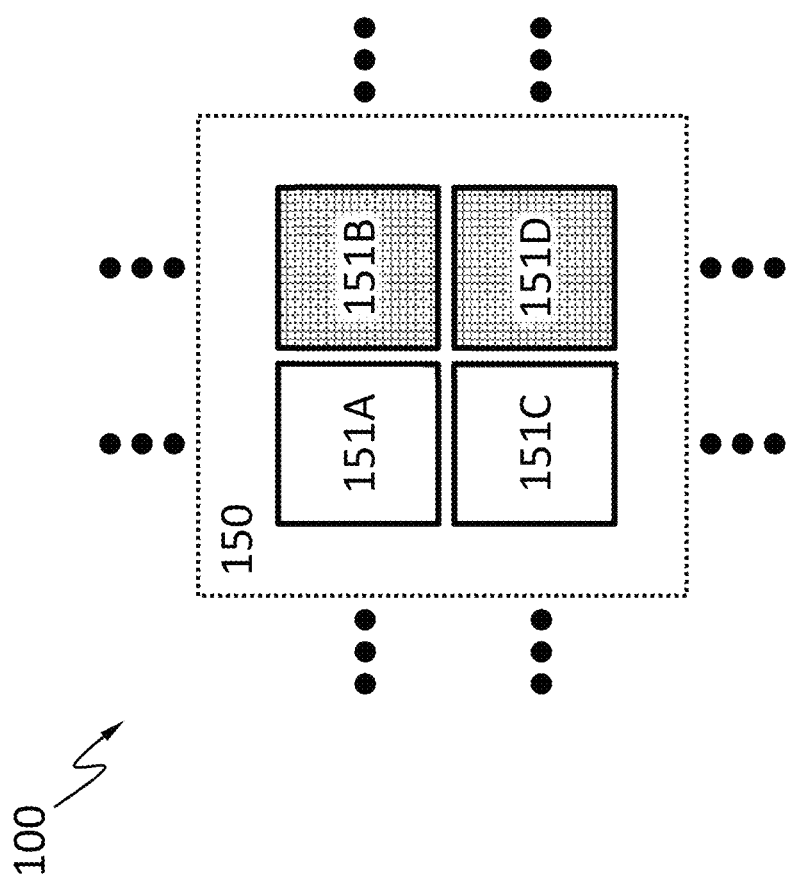
FIG. 2 schematically shows a top view of the detector, according to an embodiment.

FIG. 2 schematically shows a top view of the detector 100, according to an embodiment. The detector 100 may have an array of pixels 150. The array may be a rectangular array, a honeycomb array, a hexagonal array or any other suitable array. At least one of the pixels 150 includes several subpixels. In the example shown in FIG. 2, a pixel 150 includes a first subpixel 151A, a second subpixel 151B, optionally a third subpixel 151C, and optionally a fourth subpixel 151D. The subpixels may be arranged in any suitable pattern. For example, the first subpixel 151A abuts the second subpixel 151B. The subpixels may generate electrical signals upon exposure to radiation. For example, the first subpixel 151A may generate a first electrical signal upon exposure to radiation; the second subpixel 151B may generate a second electrical signal upon exposure to radiation. The first electrical signal may be a voltage of the electric contact 119B. The detector 100 may determine the number of particles of radiation incident on the first subpixel 151A over a first period of time, based on the first electrical signal. The detector 100 may measure energies of the particles of the radiation incident on the first subpixel 151A, based on the first electrical signal. For example, the detector 100 has an analog-to-digital converter (ADC) configured to digitize an analog signal from the first subpixel 151A that represents the energy of an incident particle of radiation into a digital signal. The ADC may have a resolution of 10 bits or higher. The detector 100 may determine (e.g., using an integrator) an intensity of the radiation by integrating the second electrical signals over a second period of time. The first period of time and the second period of time may or may not be the same.

The first subpixel 151A and the second subpixel 151B may operate in parallel. The first period of time and the second period of time may overlap by any degree or not overlap at all. For example, the first period of time may begin or end during, before or after the second period of time; the second period of time may begin or end during, before or after the first period of time. The first time period and the second time period may be the same. The subpixels 151A and 151B may be but do not have to be individually addressable.

If the pixel 150 includes the third subpixel 150C, the third subpixel 151C may generate a third electrical signal upon exposure to radiation. The detector 100 may determine a number of particles of the radiation incident on the third subpixel over the first period of time, based on the third electrical signal. The detector 100 may measure energies of the particles of the radiation incident on the third subpixel 151C, based on the third electrical signal.

The detector 100 may optionally include additional (e.g., 10, 100, 1000, 10000, or more) subpixels that generate electrical signals the detector 100 may use to determine the numbers of particles of the radiation incident on these additional subpixels (e.g., over the first period of time) or the energies of these particles. The detector 100 may determine the sum of the numbers of particles of radiation incident on the first subpixels 151A, the third subpixels 151C, and optionally these additional subpixels. If the detector 100 can determine the energies of these particles, the detector 100 may determine a sum of the numbers of those among the particles of radiation that have energies in a certain range. For example, the detector 100 may determine respectively the total numbers of particles incident on the first subpixel 151A and the third subpixels 151C and whose energies are from 70 KeV to 71 KeV, from 71 KeV to 72 KeV, and so on.

The detector 100 may compile these total numbers into an energy spectrum of the radiation incident on the detector 100, over a period of time.

If the pixel 150 includes the fourth subpixel 150D, the fourth subpixel 151D may generate a fourth electrical signal upon exposure to radiation. The detector 100 may determine (e.g., using an integrator) an intensity of the radiation by integrating the fourth electrical signals over the second period of time. The detector 100 may determine the intensity of the radiation by integrating the second electrical signal and the fourth electrical signal over the second period of time.

The detector 100 may optionally include additional (e.g., 10, 100, 1000, 10000, or more) subpixels that generate electrical signals the detector 100 may integrate (e.g., over the second period of time) to determine the intensity of the radiation. The detector 100 may integrate the sum of these electrical signals or compute the sum of the integrations of these signals.

Figure 3:
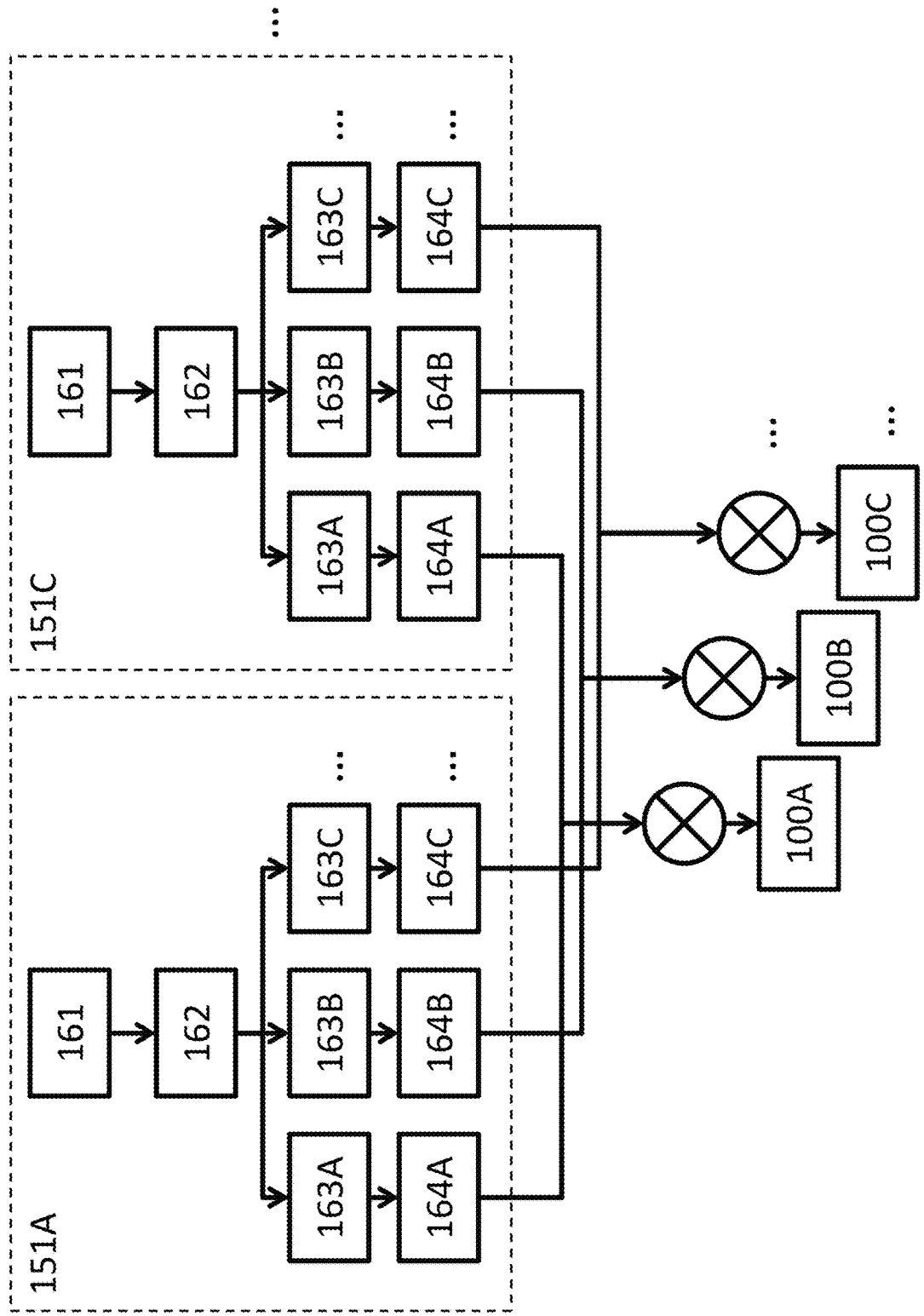
FIG. 3 schematically shows a block diagram for the detector, according to an embodiment.

FIG. 3 schematically shows a block diagram for the detector 100, according to an embodiment. The first subpixel 151A and the third subpixel 151C each measure the energies 161 of multiple particles of radiation incident thereon. The particles of radiation are allocated in step 162 into one of a plurality of bins 163A, 163B, 163C . . . based on the energies 161. The bins 163A, 163B, 163C . . . each have a corresponding counter 164A, 164B and 164C, respectively. When one of the particles is allocated into a bin, the number stored in the corresponding counter increases by one.

Figure 4:
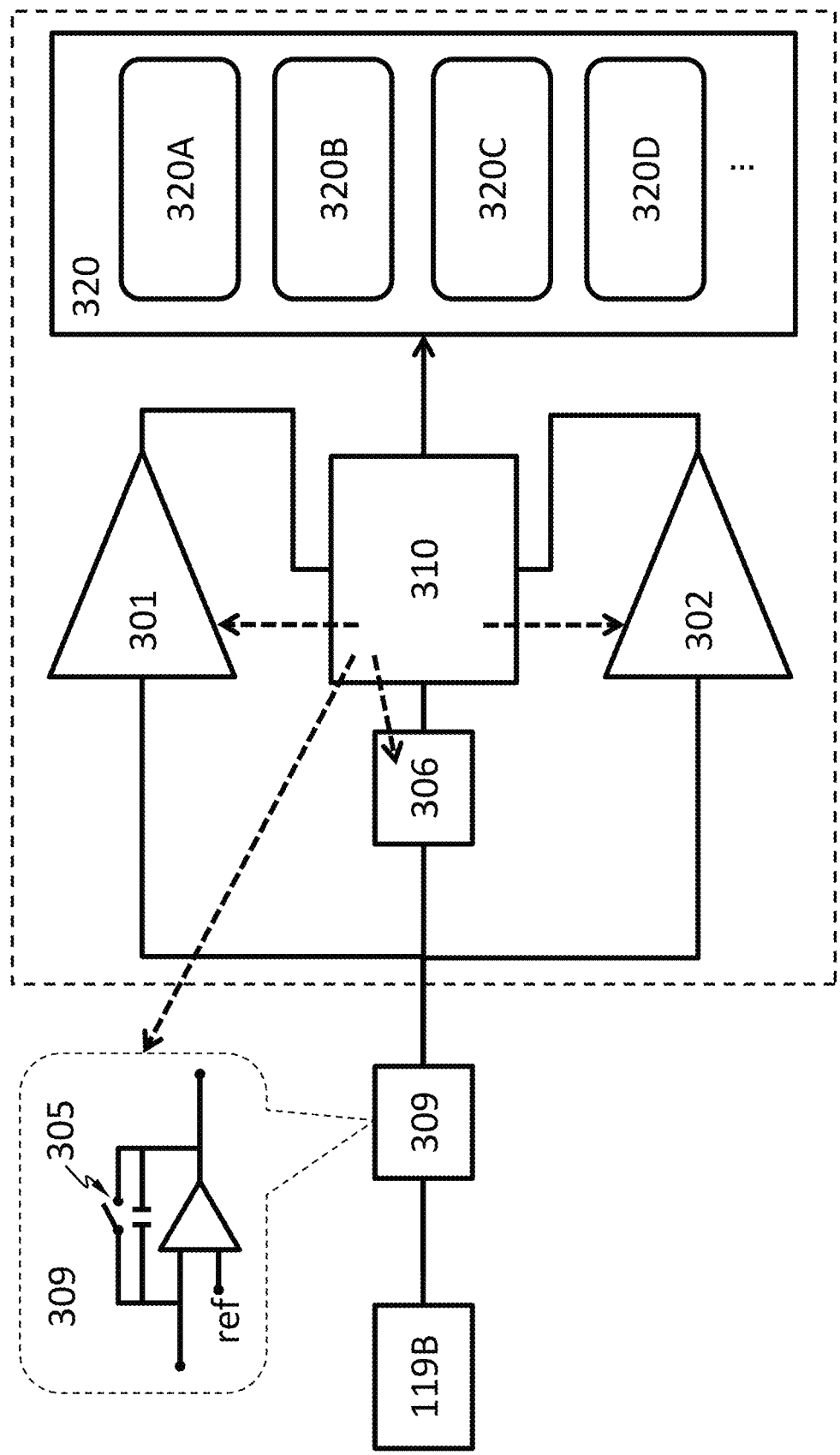
FIG. 4 schematically shows a functional block diagram of the electronic system of the radiation detector, according to an embodiment.

FIG. 4 shows a component diagram of the electronic system 121, according to an embodiment. The electronic system 121 may be used to process or interpret signals from the first subpixel 151A or the third subpixel 151C. The electronic system 121 may include a first voltage comparator 301, a second voltage comparator 302, a plurality of counters 320 (e.g., counters 320A, 320B, 320C, 320D . . . ), an ADC 306, an integrator 309, and a controller 310.

The first voltage comparator 301 is configured to compare the voltage of a discrete portion of the electric contact 119B to a first threshold. The first voltage comparator 301 may be configured to monitor the voltage directly, or calculate the voltage by integrating an electric current flowing through the diode or electric contact over a period of time. The first voltage comparator 301 may be controllably activated or deactivated by the controller 310. The first voltage comparator 301 may be a continuous comparator. Namely, the first voltage comparator 301 may be configured to be activated continuously, and monitor the voltage continuously. The first voltage comparator 301 configured as a continuous comparator reduces the chance that the system 121 misses signals generated by an incident particle of radiation. The first voltage comparator 301 configured as a continuous comparator is especially suitable when the incident radiation intensity is relatively high. The first voltage comparator 301 may be a clocked comparator, which has the benefit of lower power consumption. The first voltage comparator 301 configured as a clocked comparator may cause the system 121 to miss signals generated by some incident particles of radiation. When the incident radiation intensity is low, the chance of missing an incident particle of radiation is low because the time interval between two successive particles of radiation is relatively long. Therefore, the first voltage comparator 301 configured as a clocked comparator is especially suitable when the incident radiation intensity is relatively low. The first threshold may be 1-5%, 5-10%, 10%-20%, 20-30%, 30-40% or 40-50% of the maximum voltage one incident particle of radiation may generate on the electric contact 119B. The maximum voltage may depend on the energy of the incident particle of radiation (i.e., the wavelength of the incident radiation), the material of the radiation absorption layer 110, and other factors. For example, the first threshold may be 50 mV, 100 mV, 150 mV, or 200 mV.

The second voltage comparator 302 is configured to compare the voltage to a second threshold V2. The second voltage comparator 302 may be configured to monitor the voltage directly, or calculate the voltage by integrating an electric current flowing through the diode or the electric contact over a period of time. The second voltage comparator 302 may be a continuous comparator. The second voltage comparator 302 may be controllably activate or deactivated by the controller 310. When the second voltage comparator 302 is deactivated, the power consumption of the second voltage comparator 302 may be less than 1%, less than 5%, less than 10% or less than 20% of the power consumption when the second voltage comparator 302 is activated. The absolute value of the second threshold is greater than the absolute value of the first threshold. As used herein, the term "absolute value" or "modulus" |x| of a real number x is the non-negative value of x without regard to its sign. Namely, $$|x| = \begin{cases} x, & \text{if } x \geq 0 \\ -x, & \text{if } x \leq 0 \end{cases}.$$

The second threshold may be 200%-300% of the first threshold. For example, the second threshold may be 100 mV, 150 mV, 200 mV, 250 mV or 300 mV. The second voltage comparator 302 and the first voltage comparator 301 may be the same component. Namely, the system 121 may have one voltage comparator that can compare a voltage with two different thresholds at different times.

The first voltage comparator 301 or the second voltage comparator 302 may include one or more operational amplifiers or any other suitable circuitry. The first voltage comparator 301 or the second voltage comparator 302 may have a high speed to allow the system 121 to operate under a high flux of incident radiation. However, having a high speed is often at the cost of power consumption.

The counters 320 may be a software component (e.g., numbers stored in a computer memory) or a hardware component (e.g., 4017 IC and 7490 IC). Each counter 320 is associated with a bin for an energy range. For example, counter 320A may be associated with a bin for 70-71 KeV, counter 320B may be associated with a bin for 71-72 KeV, counter 320C may be associated with a bin for 72-73 KeV, counter 320D may be associated with a bin for 73-74 KeV. When the energy of an incident particle of radiation is determined by the ADC 306 to be in the bin a counter 320 is associated with, the number registered in the counter 320 is increased by one.

The controller 310 may be a hardware component such as a microcontroller and a microprocessor. The controller 310 is configured to start a time delay from a time at which the first voltage comparator 301 determines that the absolute value of the voltage equals or exceeds the absolute value of the first threshold (e.g., the absolute value of the voltage increases from below the absolute value of the first threshold to a value equal to or above the absolute value of the first threshold). The absolute value is used here because the voltage may be negative or positive, depending on whether the voltage of the cathode or the anode of the diode or which electric contact is used. The controller 310 may be configured to keep deactivated the second voltage comparator 302, the counter 320 and any other circuits the operation of the first voltage comparator 301 does not require, before the time at which the first voltage comparator 301 determines that the absolute value of the voltage equals or exceeds the absolute value of the first threshold. The time delay may expire after the voltage becomes stable, i.e., the rate of change of the voltage is substantially zero. The phase "the rate of change is substantially zero" means that temporal change is less than 0.1%/ns. The phase "the rate of change is substantially non-zero" means that temporal change of the voltage is at least 0.1%/ns.

The controller 310 may be configured to activate the second voltage comparator during (including the beginning and the expiration) the time delay. In an embodiment, the controller 310 is configured to activate the second voltage comparator at the beginning of the time delay. The term "activate" means causing the component to enter an operational state (e.g., by sending a signal such as a voltage pulse or a logic level, by providing power, etc.). The term "deactivate" means causing the component to enter a non-operational state (e.g., by sending a signal such as a voltage pulse or a logic level, by cut off power, etc.). The operational state may have higher power consumption (e.g., 10 times higher, 100 times higher, 1000 times higher) than the non-operational state. The controller 310 itself may be deactivated until the output of the first voltage comparator 301 activates the controller 310 when the absolute value of the voltage equals or exceeds the absolute value of the first threshold.

The controller 310 may be configured to cause the number registered by one of the counters 320 to increase by one, if, during the time delay, the second voltage comparator 302 determines that the absolute value of the voltage equals or exceeds the absolute value of the second threshold, and the energy of the particle of radiation falls in the bin associated with the counter 320.

The controller 310 may be configured to cause the ADC 306 to digitize the voltage upon expiration of the time delay and determine based on the voltage which bin the energy of the particle of radiation falls in.

The controller 310 may be configured to connect the electric contact 119B to an electrical ground, so as to reset the voltage and discharge any charge carriers accumulated on the electric contact 119B. In an embodiment, the electric contact 119B is connected to an electrical ground after the expiration of the time delay. In an embodiment, the electric contact 119B is connected to an electrical ground for a finite reset time period. The controller 310 may connect the electric contact 119B to the electrical ground by controlling a switch 305 in the integrator 309. The switch may be a transistor such as a field-effect transistor (FET).

In an embodiment, the system 121 has no analog filter network (e.g., a RC network). In an embodiment, the system 121 has no analog circuitry.

The ADC 306 may feed the voltage it measures to the controller 310 as an analog or digital signal. The ADC may be a successive-approximation-register (SAR) ADC (also called successive approximation ADC). An SAR ADC digitizes an analog signal via a binary search through all possible quantization levels before finally converging upon a digital output for the analog signal. An SAR ADC may have four main subcircuits: a sample and hold circuit to acquire the input voltage ($V_{in}$), an internal digital-analog converter (DAC) configured to supply an analog voltage comparator with an analog voltage equal to the digital code output of the successive approximation register (SAR), the analog voltage comparator that compares $V_{in}$ to the output of the internal DAC and outputs the result of the comparison to the SAR, the SAR configured to supply an approximate digital code of $V_{in}$ to the internal DAC. The SAR may be initialized so that the most significant bit (MSB) is equal to a digital 1. This code is fed into the internal DAC, which then supplies the analog equivalent of this digital code ($V_{ref}/2$) into the comparator for comparison with $V_{in}$. If this analog voltage exceeds $V_{in}$ the comparator causes the SAR to reset this bit; otherwise, the bit is left a 1. Then the next bit of the SAR is set to 1 and the same test is done, continuing this binary search until every bit in the SAR has been tested. The resulting code is the digital approximation of $V_{in}$ and is finally output by the SAR at the end of the digitization.

The system 121 may include an operational amplifier integrator 309 electrically connected to the electric contact 119B, wherein the integrator 309 is configured to integrate electrical signals from the electric contacts 119B of the second subpixel 151B or the electric contacts 119B of the fourth subpixel 151D, over the second period of time. The integrator 309 can include a capacitor in the feedback path of the operational amplifier. The operational amplifier configured as such is called a capacitive transimpedance amplifier (CTIA). CTIA has high dynamic range by keeping the operational amplifier from saturating and improves the signal-to-noise ratio by limiting the bandwidth in the signal path. Charge carriers from the electric contact accumulate on the capacitor over a period of time ("integration period"). After the integration period has expired, the capacitor voltage is sampled by the ADC 306 and then reset by a reset switch. The integrator 309 can include a capacitor directly connected to the electric contact 119B.

Figure 5:
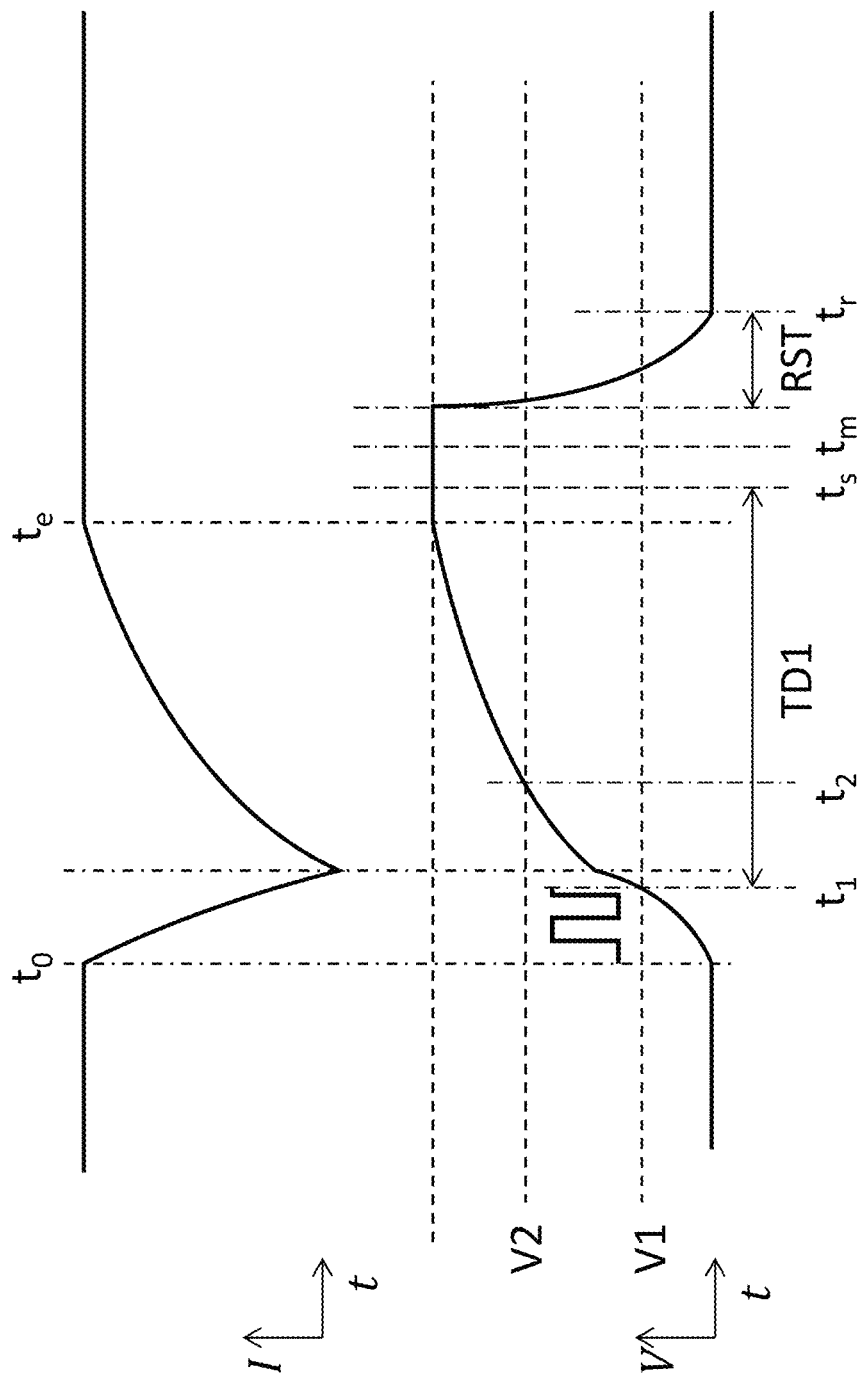
FIG. 5 and FIG. 6 each schematically shows a temporal change of the electric current flowing through an electric contact (upper curve) of a subpixel exposed to radiation, the electric current caused by charge carriers generated by particles of radiation incident on the radiation absorption layer, and a corresponding temporal change of the voltage of the electric contact (lower curve), according to an embodiment.

FIG. 5 schematically shows a temporal change of the electric current flowing through the electric contact 119B (upper curve) of the first subpixel 151A or the third subpixel 151C caused by charge carriers generated by a particle of radiation incident on the subpixels associated with the electric contact 119B, and a corresponding temporal change of the voltage of the electric contact 119B (lower curve). The voltage may be an integral of the electric current with respect to time. At time $t_0$, the particle of radiation hits the diode or the resistor, charge carriers start being generated in the pixel 150, electric current starts to flow through the electric contact 119B, and the absolute value of the voltage of the electric contact 119B starts to increase. At time $t_1$, the first voltage comparator 301 determines that the absolute value of the voltage equals or exceeds the absolute value of the first threshold V1, and the controller 310 starts the time delay TD1 and the controller 310 may deactivate the first voltage comparator 301 at the beginning of TD1. If the controller 310 is deactivated before $t_1$, the controller 310 is activated at $t_1$. During TD1, the controller 310 activates the second voltage comparator 302. The term "during" a time delay as used here means the beginning and the expiration (i.e., the end) and any time in between. For example, the controller 310 may activate the second voltage comparator 302 at the expiration of TD1. If during TD1, the second voltage comparator 302 determines that the absolute value of the voltage equals or exceeds the absolute value of the second threshold at time $t_2$, the controller 310 waits for stabilization of the voltage to stabilize. The voltage stabilizes at time $t_e$, when all charge carriers generated by the particle of radiation drift out of the radiation absorption layer 110. At time $t_s$, the time delay TD1 expires. At or after time $t_e$, the controller 310 causes the ADC 306 to digitize the voltage and determines which bin the energy of the particles of radiation falls in. The controller 310 then causes the number registered by the counter 320 corresponding to the bin to increase by one. In the example of FIG. 5, time $t_s$ is after time $t_e$; namely TD1 expires after all charge carriers generated by the particle of radiation drift out of the radiation absorption layer 110. If time $t_e$ cannot be easily measured, TD1 can be empirically chosen to allow sufficient time to collect essentially all charge carriers generated by a particle of radiation but not too long to risk have another incident particle of radiation. Namely, TD1 can be empirically chosen so that time $t_s$ is empirically after time $t_e$. Time $t_s$ is not necessarily after time $t_e$ because the controller 310 may disregard TD1 once V2 is reached and wait for time $t_e$. The rate of change of the difference between the voltage and the contribution to the voltage by the dark current is thus substantially zero at $t_e$. The controller 310 may be configured to deactivate the second voltage comparator 302 at expiration of TD1 or at $t_2$, or any time in between.

The voltage at time $t_e$ is proportional to the amount of charge carriers generated by the particle of radiation, which relates to the energy of the particle of radiation. The controller 310 may be configured to determine the bin the energy of the particle of radiation falls in, based on the output of the ADC 306.

After TD1 expires or digitization by the ADC 306, whichever later, the controller 310 connects the electric contact 119B to an electric ground for a reset period RST to allow charge carriers accumulated on the electric contact 119B to flow to the ground and reset the voltage. After RST, the system 121 is ready to detect another incident particle of radiation. Implicitly, the rate of incident particles of radiation the system 121 can handle in the example of FIG. 5 is limited by 1/(TD1+RST). If the first voltage comparator 301 has been deactivated, the controller 310 can activate it at any time before RST expires. If the controller 310 has been deactivated, it may be activated before RST expires.

Figure 6:
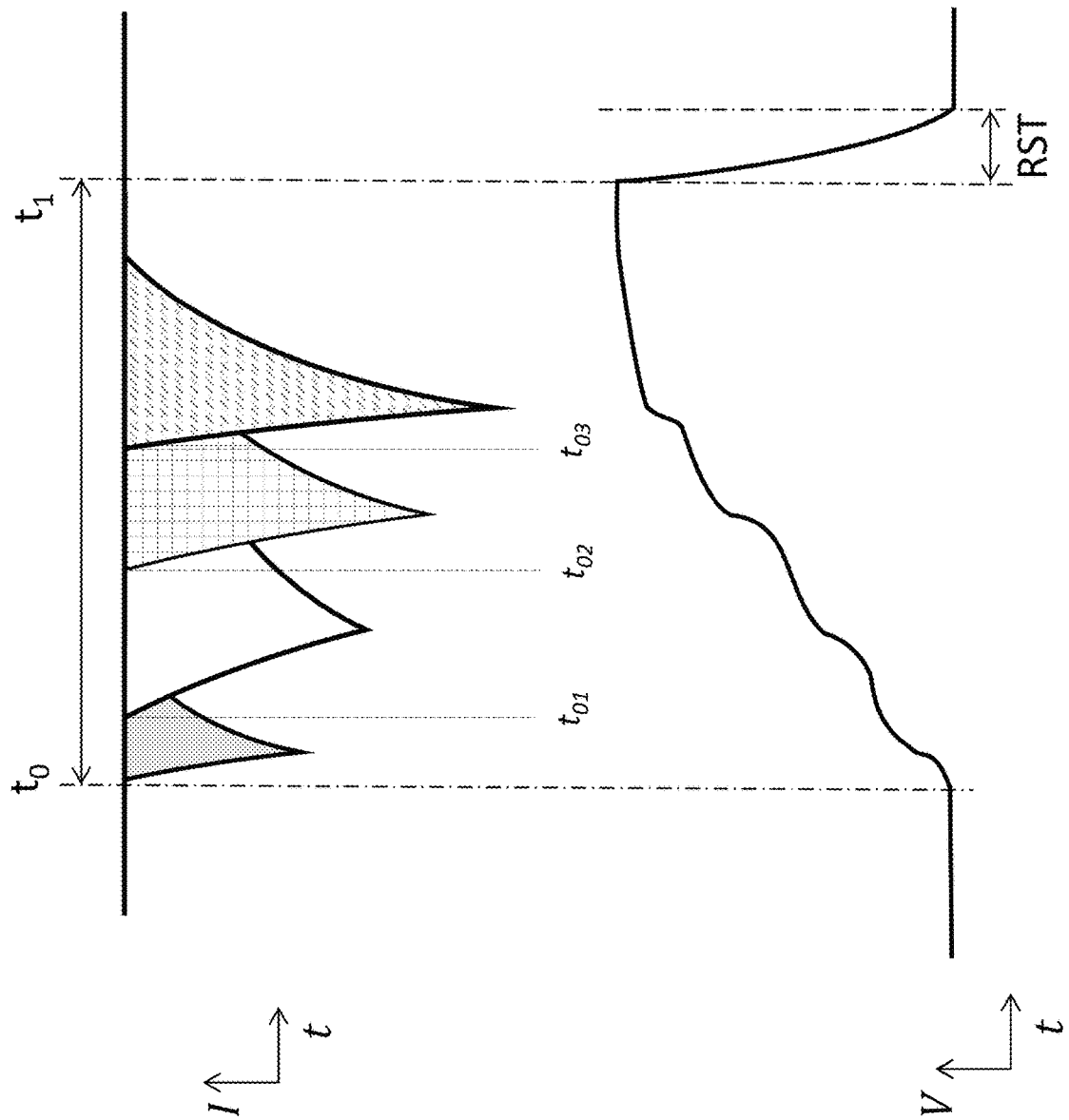

FIG. 6 schematically shows a temporal change (upper curve) of the electric current flowing from the electric contact 119B associated with the second subpixel 151B (or the fourth subpixel 151D). The electric current is caused by charge carriers generated by particles of radiation incident on the subpixel 151B (or 151D). FIG. 6 also schematically shows a corresponding temporal change (lower curve) of the voltage of the electric contact 119B. The voltage may be an integral of the electric current with respect to time. At time $t_0$, a first particle of radiation hits the second subpixel 151B (or the fourth subpixel 151D), charge carriers start being generated in radiation absorption layer 110, electric current starts to flow from the electric contact 119B, and the absolute value of the voltage of the electric contact 119B starts to increase. At time $t_{01}$, a second particle of radiation hits the second subpixel 151B (or the fourth subpixel 151D), more charge carriers are generated in radiation absorption layer 110, and more electric current flows from the electric contact 119B, and the absolute value of the voltage of the electric contact 119B increases further. During the integration period ($t_0$ to $t_1$), more particles of radiations may hit the second subpixel 151B (or the fourth subpixel 151D). In the example in FIG. 6, at time $t_{02}$ and $t_{03}$, two more particles of radiation respectively hit the second subpixel 151B (or the fourth subpixel 151D), and the voltage of the electric contact 119B increases even further. The electric current is integrated over the period from $t_0$ to $t_1$.

After $t_1$, the voltage of the electric contact 119B is measured and this voltage represents the intensity of the radiation incident on the second subpixel 151B (or the fourth subpixel 151D). The electric contact 119B may be connected to an electric ground for a reset period RST to allow charge carriers accumulated on the electric contact 119B to flow to the ground and reset the voltage.

Figure 7:
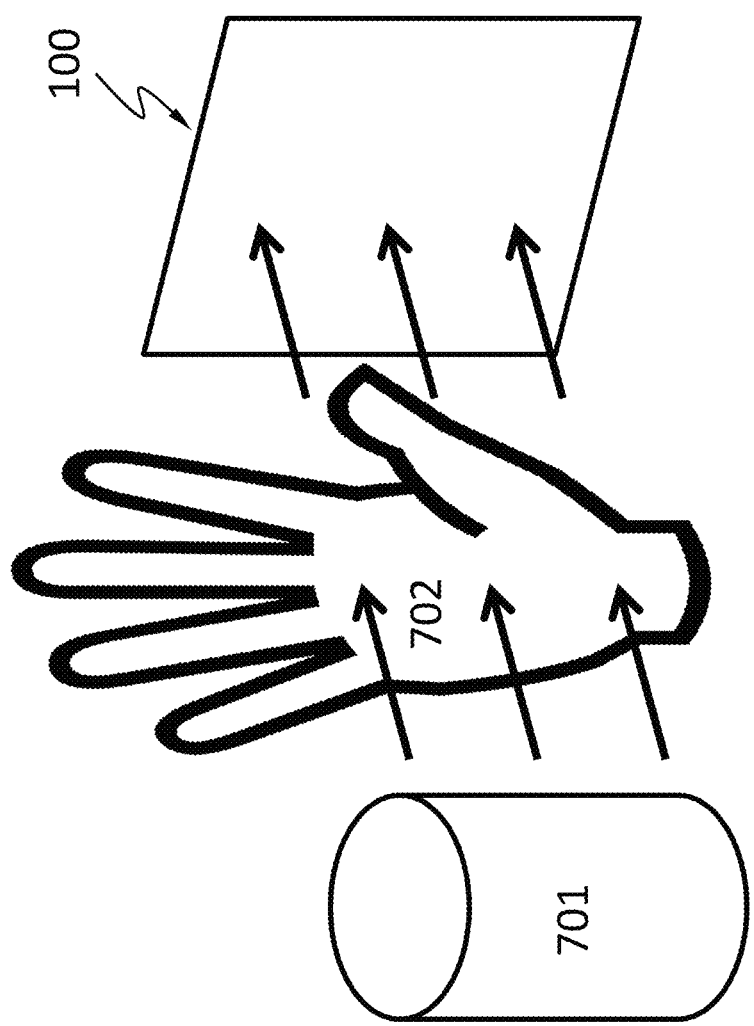
FIG. 7-FIG. 12 each schematically shows a system comprising the detector described herein.

FIG. 7 schematically shows a system comprising the detector 100 described herein. The system may be used for medical imaging such as chest radiation radiography, abdominal radiation radiography, dental radiation radiography, etc. The system comprises a radiation source 701. radiation emitted from the radiation source 701 penetrates an object 702 (e.g., a human body part such as chest, limb, abdomen, mouth), is attenuated by different degrees by the internal structures of the object 702 (e.g., bones, muscle, fat, organs and teeth, etc.), and is projected to the detector 100. The detector 100 forms an image by detecting the intensity distribution of the radiation.

Figure 8:
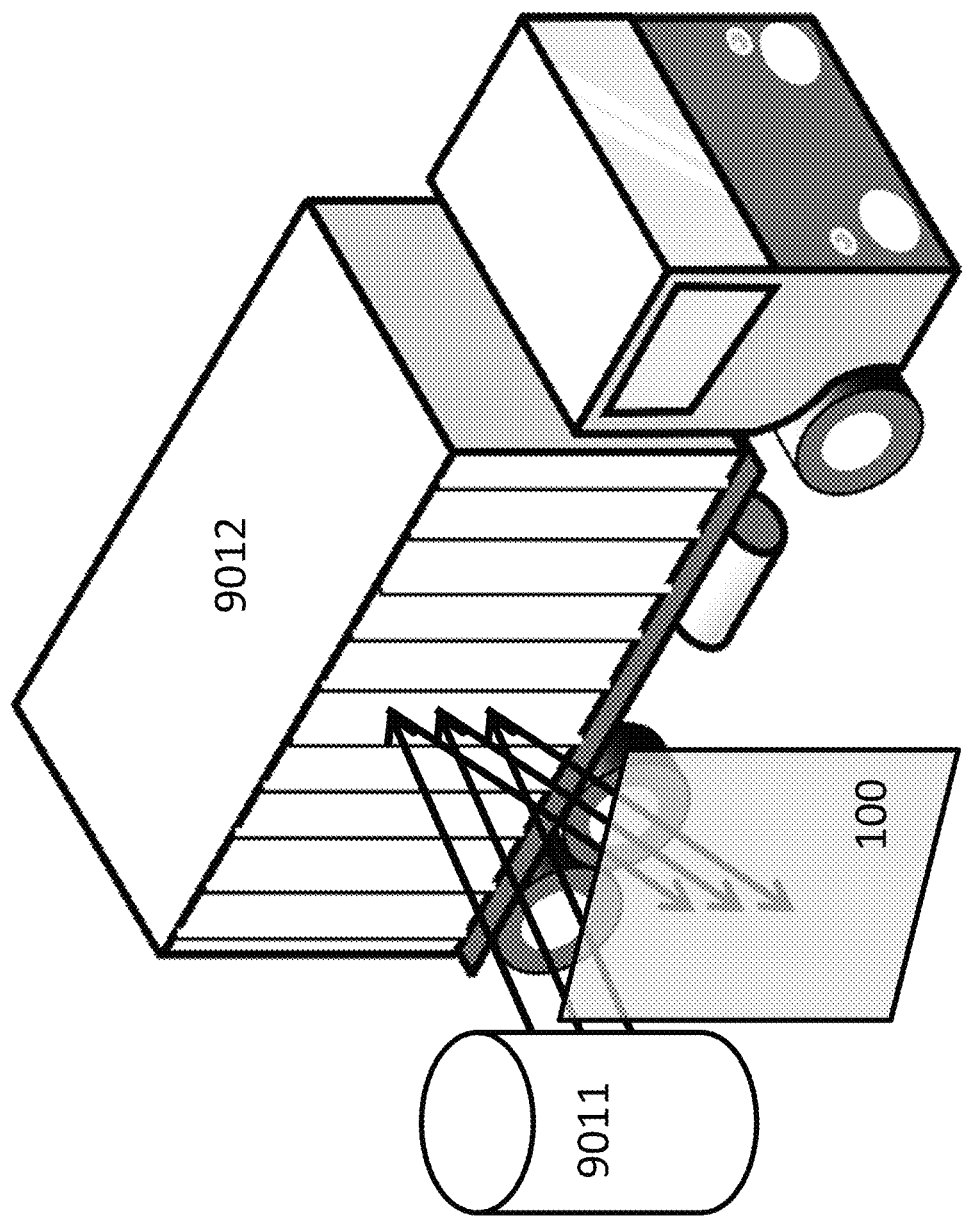

FIG. 8 schematically shows a cargo scanning or non-intrusive inspection (NII) system comprising the detector 100 described herein. The system may be used for inspecting and identifying goods in transportation systems such as shipping containers, vehicles, ships, luggage, etc. The system comprises a radiation source 9011. radiation emitted from the radiation source 9011 may backscatter from an object 9012 (e.g., shipping containers, vehicles, ships, etc.) and be projected to the detector 100. Different internal structures of the object 9012 may backscatter radiation differently. The detector 100 forms an image by detecting the intensity distribution of the backscattered radiation and/or energies of the backscattered particles of radiation.

Figure 9:
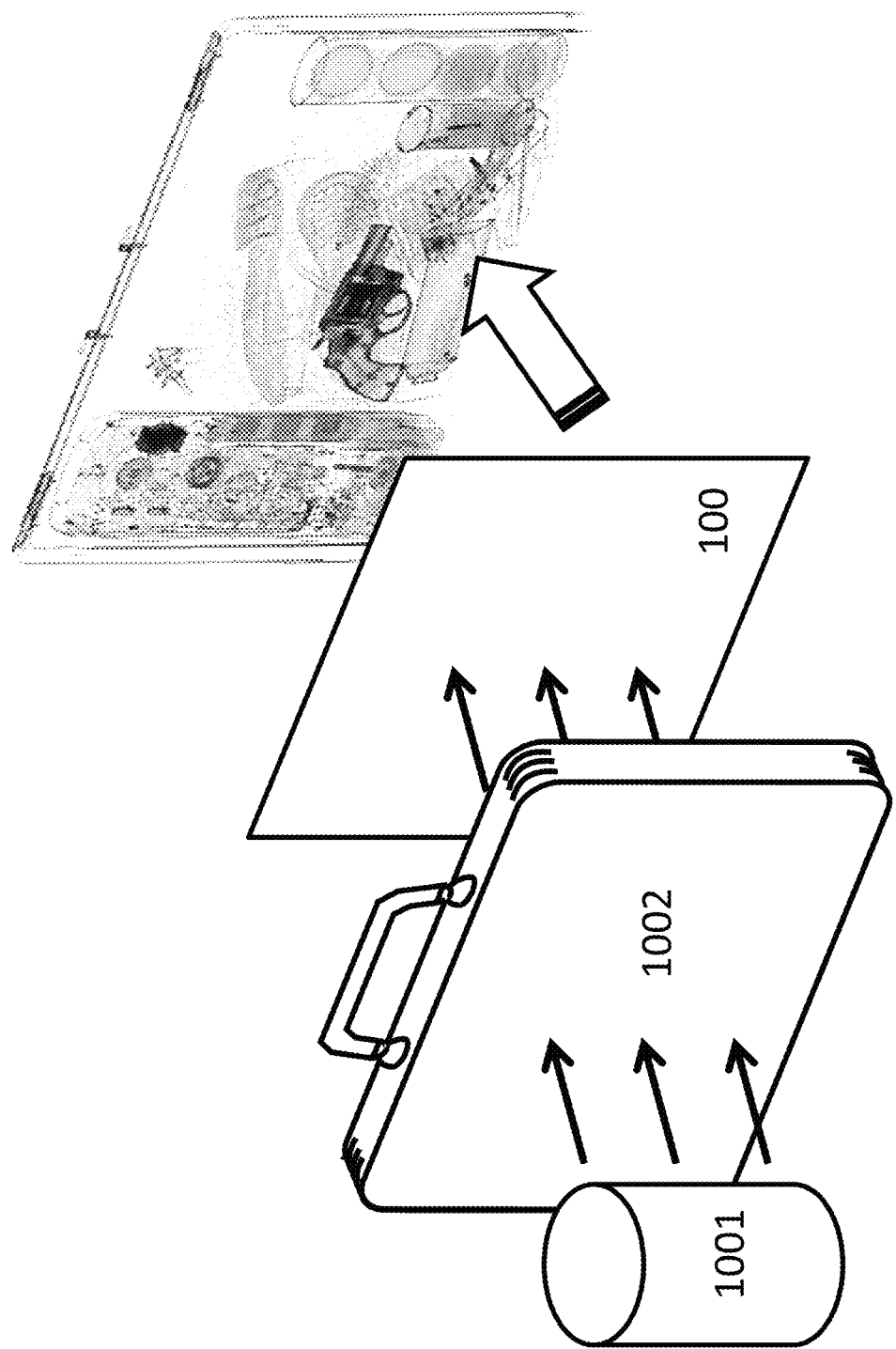

FIG. 9 schematically shows another cargo scanning or non-intrusive inspection (NII) system comprising the detector 100 described herein. The system may be used for luggage screening at public transportation stations and airports. The system comprises a radiation source 1001. radiation emitted from the radiation source 1001 may penetrate a piece of luggage 1002, be differently attenuated by the contents of the luggage, and projected to the detector 100. The detector 100 forms an image by detecting the intensity distribution of the transmitted radiation. The system may reveal contents of luggage and identify items forbidden on public transportation, such as firearms, narcotics, edged weapons, flammables.

Figure 10:
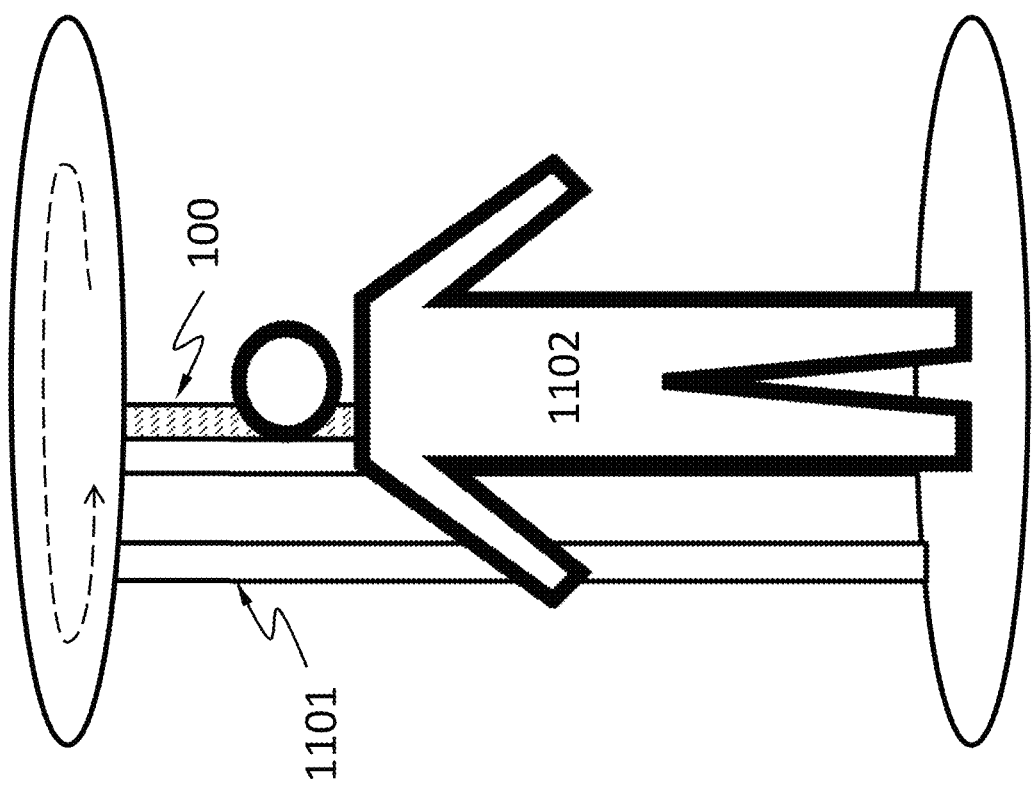

FIG. 10 schematically shows a full-body scanner system comprising the detector 100 described herein. The full-body scanner system may detect objects on a person's body for security screening purposes, without physically removing clothes or making physical contact. The full-body scanner system may be able to detect non-metal objects. The full-body scanner system comprises a radiation source 1101. radiation emitted from the radiation source 1101 may backscatter from a human 1102 being screened and objects thereon, and be projected to the detector 100. The objects and the human body may backscatter radiation differently. The detector 100 forms an image by detecting the intensity distribution of the backscattered radiation. The detector 100 and the radiation source 1101 may be configured to scan the human in a linear or rotational direction.

Figure 11:
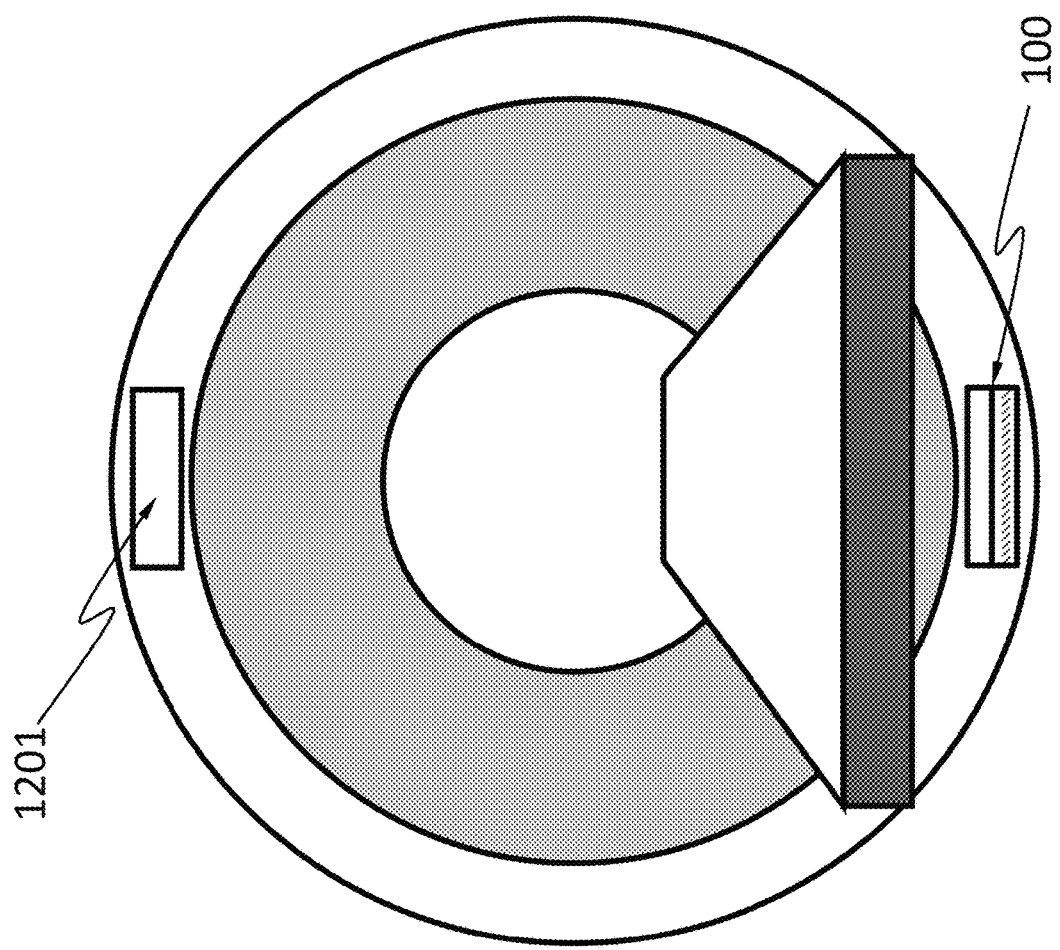

FIG. 11 schematically shows a radiation computed tomography (radiation CT) system comprising the detector 100 described herein. The radiation CT system uses computer-processed radiation to produce tomographic images (virtual "slices") of specific areas of a scanned object. The tomographic images may be used for diagnostic and therapeutic purposes in various medical disciplines, or for flaw detection, failure analysis, metrology, assembly analysis and reverse engineering. The radiation CT system comprises the detector 100 described herein and a radiation source 1201.

The detector 100 and the radiation source 1201 may be configured to rotate synchronously along one or more circular or spiral paths.

Figure 12:
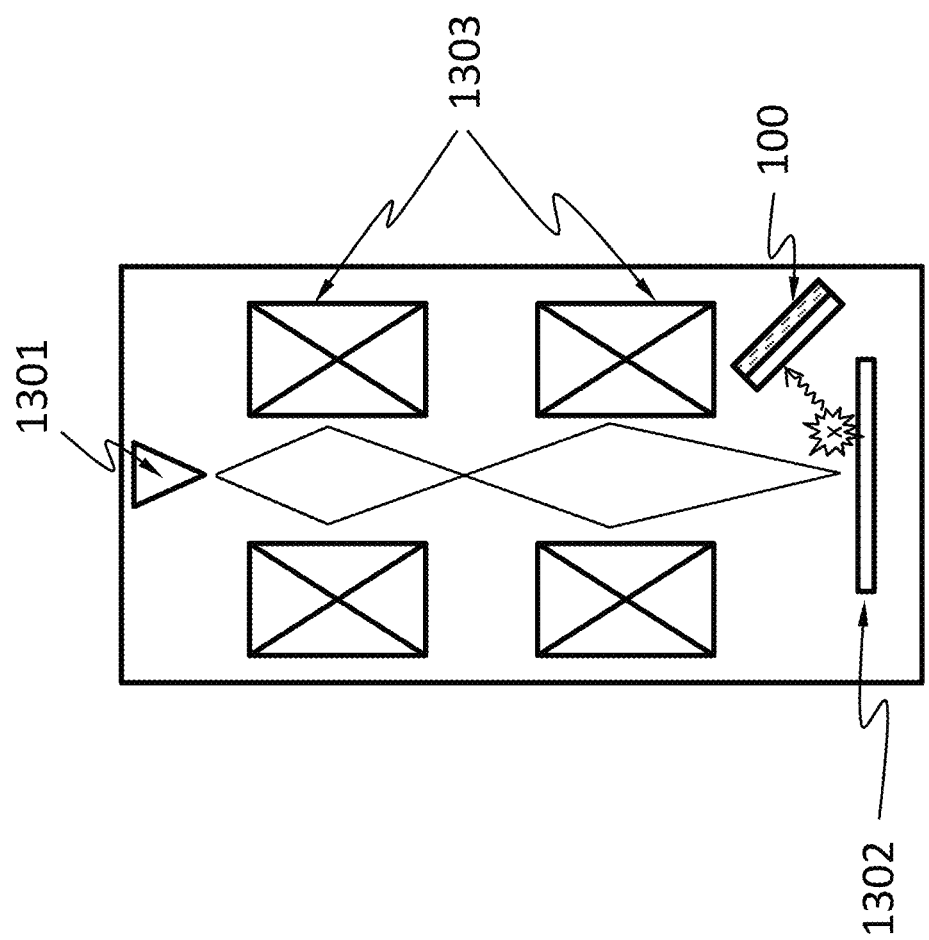

FIG. 12 schematically shows an electron microscope comprising the detector 100 described herein. The electron microscope comprises an electron source 1301 (also called an electron gun) that is configured to emit electrons. The electron source 1301 may have various emission mechanisms such as thermionic, photocathode, cold emission, or plasmas source. The emitted electrons pass through an electronic optical system 1303, which may be configured to shape, accelerate, or focus the electrons. The electrons then reach a sample 1302 and an image detector may form an image therefrom. The electron microscope may comprise the detector 100 described herein, for performing energy-dispersive radiation spectroscopy (EDS). EDS is an analytical technique used for the elemental analysis or chemical characterization of a sample. When the electrons incident on a sample, they cause emission of characteristic radiation from the sample. The incident electrons may excite an electron in an inner shell of an atom in the sample, ejecting it from the shell while creating an electron hole where the electron was. An electron from an outer, higher-energy shell then fills the hole, and the difference in energy between the higher-energy shell and the lower energy shell may be released in the form of a radiation. The number and energy of the radiation emitted from the sample can be measured by the detector 100.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A detector comprising:
a pixel comprising a first subpixel and a second subpixel, wherein the first subpixel is configured to generate a first electrical signal upon exposure to radiation, and wherein the second subpixel is configured to generate a second electrical signal upon exposure to the radiation;
wherein the detector is configured to determine a number of particles of the radiation incident on the first subpixel over a first period of time, based on the first electrical signal;
wherein the detector is configured to determine an intensity of the radiation by integrating the second electrical signal over a second period of time.

2. The detector of claim 1, wherein the first period of time and the second period of time are the same.

3. The detector of claim 1, wherein the first subpixel abuts the second subpixel.

4. The detector of claim 1, wherein the detector is configured to measure energies of the particles of the radiation incident on the first subpixel, based on the first electrical signal.

5. The detector of claim 4, wherein the detector is configured to determine an energy spectrum of the radiation based on the energies of the particles of the radiation.

6. The detector of claim 4, wherein the first subpixel comprises a radiation absorption layer and an electric contact; and wherein the first electrical signal is a voltage of the electric contact.

7. The detector of claim 6, further comprising:
a first voltage comparator configured to compare the voltage to a first threshold;
a second voltage comparator configured to compare the voltage to a second threshold;
a counter configured to register the number of the particles of the radiation;
a controller;
wherein the controller is configured to start a time delay from a time at which the first voltage comparator determines that an absolute value of the voltage equals or exceeds an absolute value of the first threshold;
wherein the controller is configured to activate the second voltage comparator during the time delay;
wherein the controller is configured to cause the number registered by the counter to increase by one, when the second voltage comparator determines that an absolute value of the voltage equals or exceeds an absolute value of the second threshold.

8. The detector of claim 7, further comprising an operational amplifier integrator electrically connected to the electric contact.

9. The detector of claim 7, wherein the controller is configured to activate the second voltage comparator at a beginning or expiration of the time delay.

10. The detector of claim 7, wherein the controller is configured to determine the energies based on a value of the voltage measured upon expiration of the time delay.

11. The detector of claim 7, wherein a rate of change of the voltage is substantially zero at expiration of the time delay.

12. The detector of claim 6, wherein the radiation absorption layer comprises a diode.

13. The detector of claim 6, wherein the radiation absorption layer comprises silicon, germanium, GaAs, CdTe, CdZnTe, or a combination thereof.

14. The detector of claim 1, wherein the pixel further comprises a third subpixel configured to generate a third electrical signal upon exposure to the radiation; and wherein the detector is configured to determine a number of particles of the radiation incident on the third subpixel over the first period of time, based on the third electrical signal.

15. The detector of claim 14, wherein the detector is configured to measure energies of the particles of the radiation incident on the third subpixel, based on the third electrical signal.

16. The detector of claim 14, wherein the detector is configured to determine a sum of the number of particles of the radiation incident on the first subpixel and the number of particles of the radiation incident on the third subpixel over the first period of time.

17. The detector of claim 1, wherein the pixel further comprises a fourth subpixel configured to generate a fourth electrical signal upon exposure to the radiation; and wherein the detector is configured to determine the intensity of the radiation by integrating the second electrical signal and the fourth electrical signal over the second period of time.

18. The detector of claim 1, the detector further comprises an integrator configured to integrate the second electrical signal.

19. The detector of claim 1, wherein the first subpixel and the second subpixel are configured to operate in parallel.

20. The detector of claim 1, wherein the detector does not comprise a scintillator.

21. A system, comprising the detector of claim 1, and a radiation source, wherein the system is configured for performing radiography on human body, limb, or teeth.

22. A cargo scanning or non-intrusive inspection (NII) system, comprising the detector of claim 1 and a radiation source, wherein the cargo scanning or non-intrusive inspection (NII) system is configured for forming an image based on backscattered radiation.

23. A cargo scanning or non-intrusive inspection (NII) system, comprising the detector of claim 1 and a radiation source, wherein the cargo scanning or non-intrusive inspection (NII) system is configured for forming an image based on radiation transmitted through an object inspected.

24. A full-body scanner system comprising the detector of claim 1 and a radiation source.

25. A radiation computed tomography (radiation CT) system comprising the detector of claim 1 and a radiation source.

26. An electron microscope comprising the detector of claim 1, an electron source and an electronic optical system.

* * * * *